(12) United States Patent
Lackey et al.

(10) Patent No.: US 9,629,937 B2
(45) Date of Patent: Apr. 25, 2017

(54) AIR SCENT DEVICE

(71) Applicants: Robert William Lackey, Hickory, NC (US); Robert Charles Beckmann, Vale, NC (US); Leslee Kim Vance, Hickory, NC (US)

(72) Inventors: Robert William Lackey, Hickory, NC (US); Robert Charles Beckmann, Vale, NC (US); Leslee Kim Vance, Hickory, NC (US)

(73) Assignee: Protect Plus Industries, LLC, Hickory, NC (US)

( * ) Notice: Subject to any disclaimer, the term of this patent is extended or adjusted under 35 U.S.C. 154(b) by 0 days.

(21) Appl. No.: 14/657,164

(22) Filed: Mar. 13, 2015

(65) Prior Publication Data

US 2015/0258235 A1    Sep. 17, 2015

Related U.S. Application Data

(60) Provisional application No. 61/952,991, filed on Mar. 14, 2014.

(51) Int. Cl.
*A61L 9/12* (2006.01)
*F16B 2/20* (2006.01)
*A61L 9/012* (2006.01)

(52) U.S. Cl.
CPC .............. *A61L 9/12* (2013.01); *A61L 9/012* (2013.01); *F16B 2/20* (2013.01)

(58) Field of Classification Search
CPC ............... A61L 9/12; A61L 9/048; F16B 2/20
USPC ..................................................... 239/34–60
See application file for complete search history.

(56) References Cited

U.S. PATENT DOCUMENTS

| 3,910,495 | A | * | 10/1975 | Cummings | A61L 9/12 |
| | | | | | 239/58 |
| 6,102,660 | A | | 8/2000 | Lee | |
| 6,117,218 | A | | 9/2000 | Snyder et al. | |
| 7,687,038 | B2 | | 3/2010 | Wheatley et al. | |
| 8,784,747 | B2 | * | 7/2014 | Carmichael | A61L 9/12 |
| | | | | | 239/34 |
| 2004/0094635 | A1 | | 5/2004 | Harris et al. | |
| 2004/0135000 | A1 | | 7/2004 | Buthier | |
| 2006/0010840 | A1 | | 1/2006 | Ashiya et al. | |
| 2007/0075159 | A1 | | 4/2007 | Lin | |
| 2009/0212124 | A1 | | 8/2009 | Kenny | |
| 2013/0175355 | A1 | * | 7/2013 | Lackey | A61L 9/12 |
| | | | | | 239/57 |
| 2014/0076989 | A1 | * | 3/2014 | Granger | A61L 9/12 |
| | | | | | 239/52 |
| 2014/0158789 | A1 | * | 6/2014 | Haymond | A61L 9/12 |
| | | | | | 239/34 |

OTHER PUBLICATIONS

International Search Report for International Application No. PCT/US15/20440 dated Jun. 22, 2015.

\* cited by examiner

*Primary Examiner* — Jason Boeckmann
(74) *Attorney, Agent, or Firm* — Clements Bernard, PLLC; Seth L. Hudson (57) ABSTRACT

The present invention provides methods and systems for an air scent device that includes a base that extends to an outer edge, an outer ring that extends substantially upward from the outer edge, and an outer lip that extends substantially outwardly from the outer ring. A plurality of protruding structures extend substantially upward from the base, and a scented substance disposed within the cavity.

17 Claims, 7 Drawing Sheets

AIR SCENT DEVICE

CROSS REFERENCE TO RELATED PATENT APPLICATION

The current application claims the benefit of the earlier priority filing date of provisional application Ser. No. 61/952,991 that was filed on Mar. 14, 2014.

FIELD OF THE INVENTION

The present invention relates generally to an air scent device containing a scented gel, and more generally relates to an air scent device that is positioned on the air entry or exit side of an air filter or within the flow of air. The device is designed to allow air to pass through or over the device, releasing the fragrance into the air stream.

BACKGROUND OF THE INVENTION

In any place where people gather there will be various odors, fragrances and the like. It is common for homeowners and businesses to oftentimes struggle to maintain pleasant smelling environments. Many odors from such various things as cooking, personal hygiene products, the presence of pets, and cigarette smoke can be present in a home or business. Odors of these types are often difficult to combat. As such, a large industry has developed dedicated to the removal and/or masking of these odors. Products such as scented sprays, odor eliminating cleaning products, fans, and air purifiers and filters are now commonly found in homes and businesses. In addition, scent dispersion products such as scented candles and electric scent dispersers are now commonly used and widely available.

Despite the wide variety of readily available devices, products, and apparatuses available to help control or eliminate odors, each and every product suffers from the same limitation, its use is localized to a particular vicinity of use. Specifically and by way of example, use of a scented spray only affects the area in which the spray is used. So, another room in the house or business will not be affected by spraying a scented spray in another room. Likewise, electric scent dispersers and candles are only able to disperse scents in the room in which they are used. If one desires to disperse scents in multiple locations or rooms, one must use a product or device in each room. This is both time consuming and expensive.

Thus, a need exists for a device or product that is able to disperse a scent into all rooms in a home or business simultaneously.

BRIEF SUMMARY OF THE INVENTION

According to an embodiment of the present invention, an air scent device includes a base that extends to an outer edge, an outer ring that extends substantially upwardly from the outer edge, an outer lip that extends substantially outwardly from the outer edge, a plurality of protruding structures extending generally upward from the base, and a scented substance disposed within the cavity.

According to another embodiment of the present invention, the air scent device includes a plurality of ridges disposed on an external surface of the outer lip.

According to yet another embodiment of the present invention, the air scent device includes a base that is generally circular.

According to yet another embodiment of the present invention, the air scent device includes at least one clip disposed within the outer lip.

According to yet another embodiment of the present invention, the air scent device includes four clips spaced an equal distance apart around the outer lip.

According to yet another embodiment of the present invention, the air scent device includes an outer lip having a top portion and a bottom portion, whereby the outer lip slopes downwardly with respect to the outer ring.

According to yet another embodiment of the present invention, the air scent device includes a clip that is engaged to a biasing member.

According to yet another embodiment of the present invention, the air scent device includes a slot within the clip.

According to yet another embodiment of the present invention, the air scent device includes a hanging mechanism comprising a first portion and a second portion, the first portion and the second portion are substantially c-shaped and the first portion is selectively secured to the second portion.

According to yet another embodiment of the present invention, an air scent device includes a base that extends to an outer edge, an outer ring that extends substantially upward from the outer edge, an outer lip that extends substantially outwardly from the outer ring, a plurality of protruding structures that extend substantially upward from the base, a clip, and a gel disposed within the cavity.

According to yet another embodiment of the present invention, the air scent device includes a gel that is dyed.

According to yet another embodiment of the present invention, the air scent device includes a gel that is scented.

According to yet another embodiment of the present invention, the air scent device includes a clip that contains raised edges.

According to yet another embodiment of the present invention, the air scent device includes a hanging mechanism comprising a first portion and a second portion, the first portion and the second portion are substantially c-shaped and the first portion is selectively secured to the second portion, wherein the first portion contains a bore and the second portion contains at least one pair of resiliently flexible fingers for insertion into the bore.

According to yet another embodiment of the present invention, the air scent device includes a protruding structure that is cylindrical in shape and has a constant diameter.

According to yet another embodiment of the present invention, the air scent device includes a circular base that extends to an outer edge, an outer ring that extends substantially upwardly from the outer edge, an outer lip that extends substantially outwardly from the outer ring, a plurality of protruding structures extending substantially upward from the base, a clip containing a biasing member for moving the clip from a first position to a second position, and a scented gel disposed within the cavity.

BRIEF DESCRIPTION OF THE DRAWINGS

The present invention is illustrated and described herein with reference to the various drawings, in which like reference numbers denote like method steps and/or system components, respectively, and in which.

DETAILED DESCRIPTION OF THE INVENTION

The present invention may be understood more readily by reference to the following detailed description of the invention taken in connection with the accompanying drawing figures, which form a part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. Any and all patents and other publications identified in this specification are incorporated by reference as though fully set forth herein.

Also, as used in the specification including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

Figure 1:
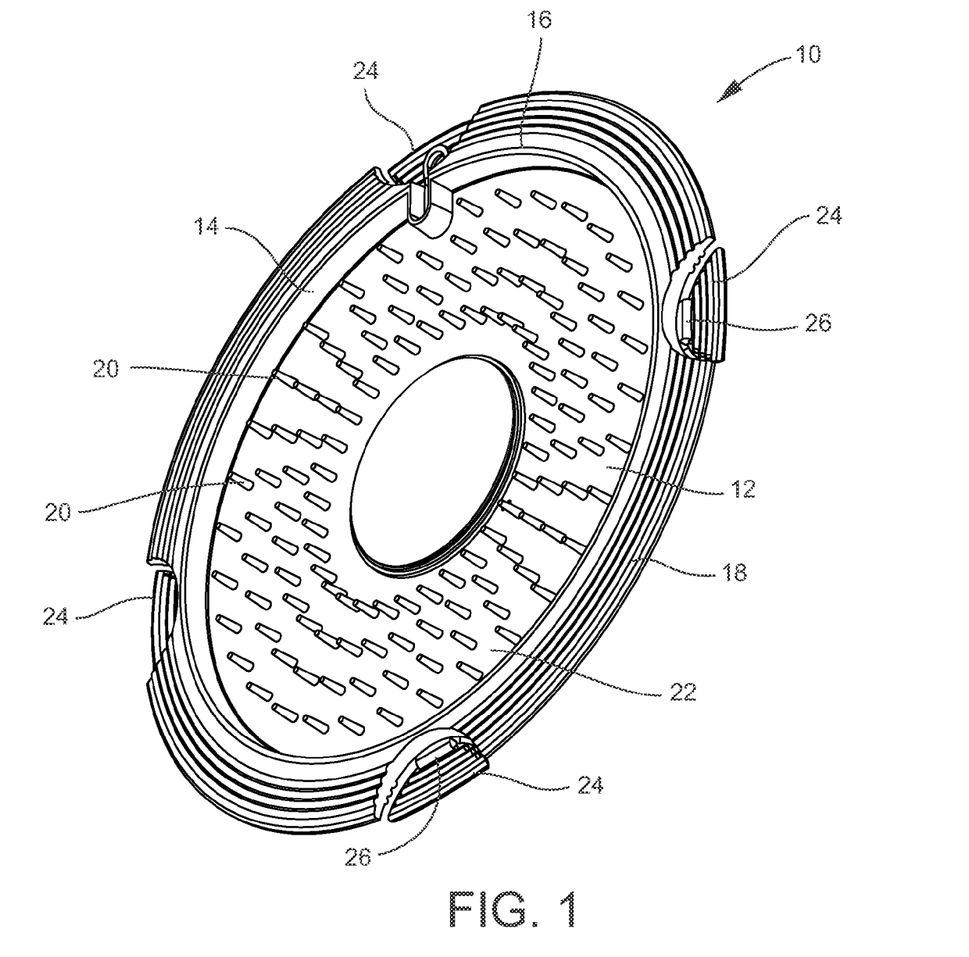
FIG. 1 is a perspective view of the present invention.
Figure 2:
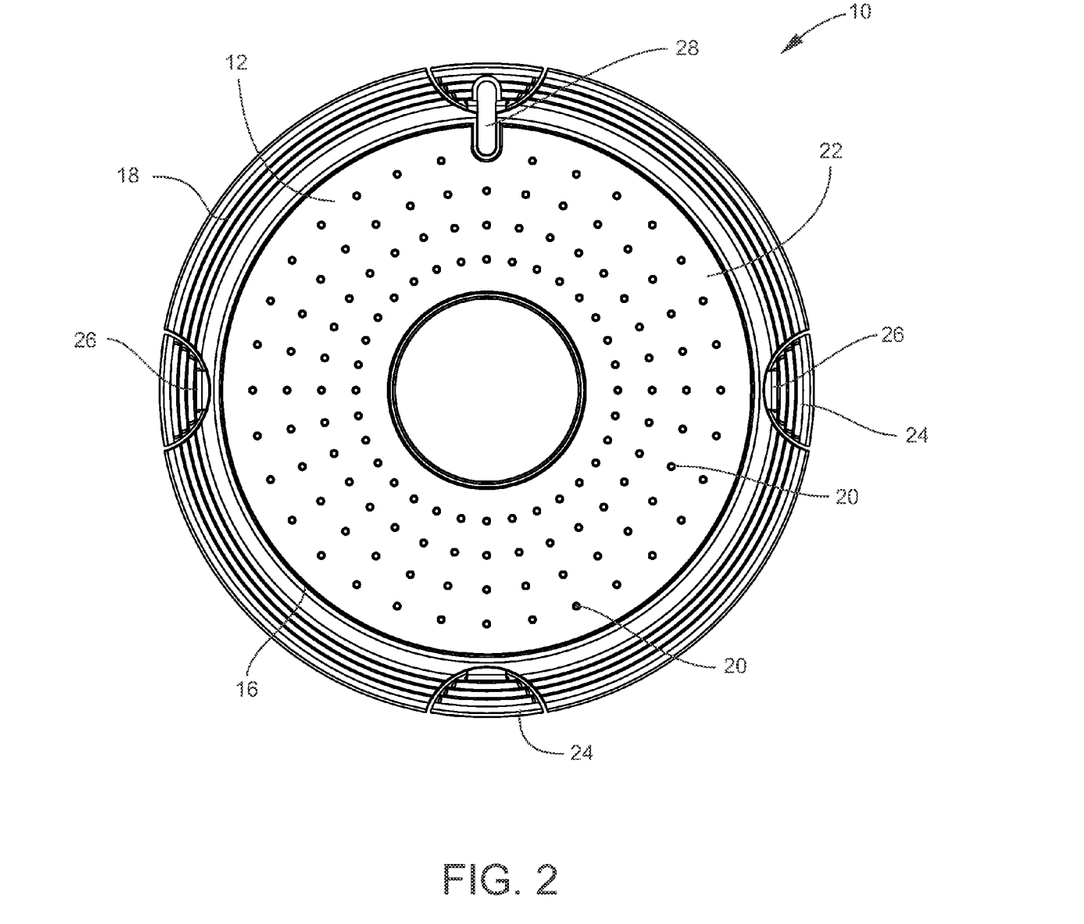
FIG. 2 is a front view of the present invention.
Figure 3:
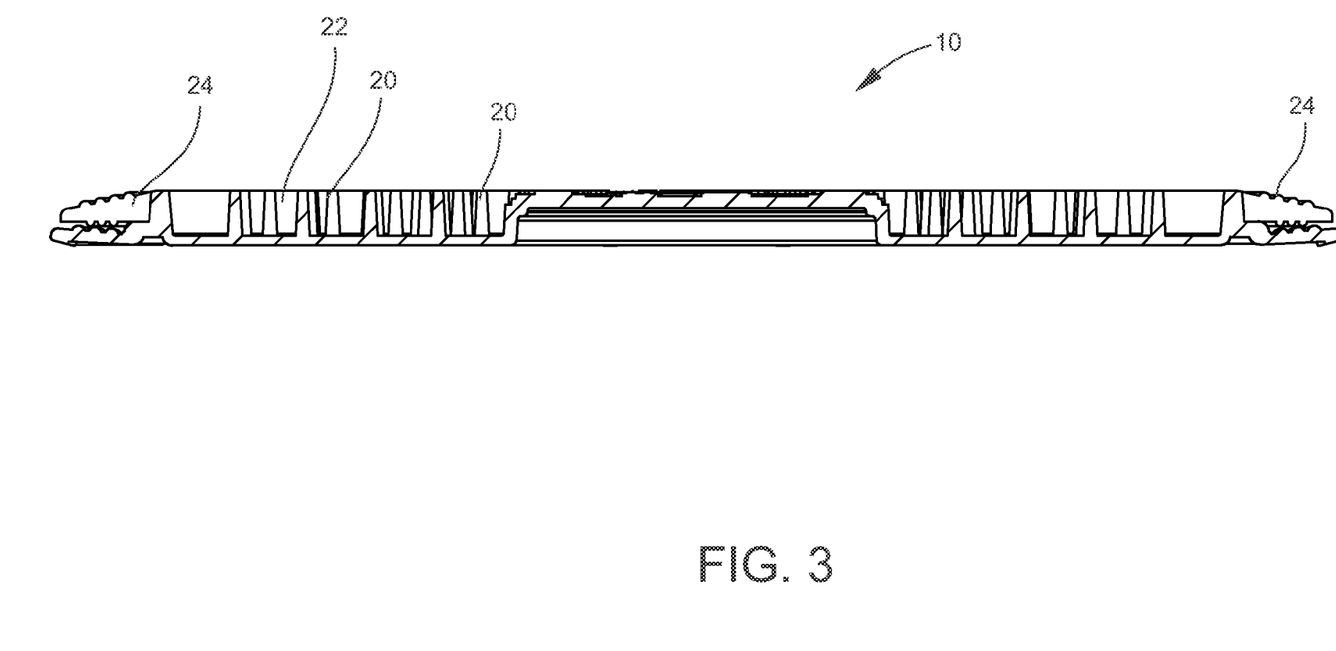
FIG. 3 is a side view of the present invention.
Figure 4:
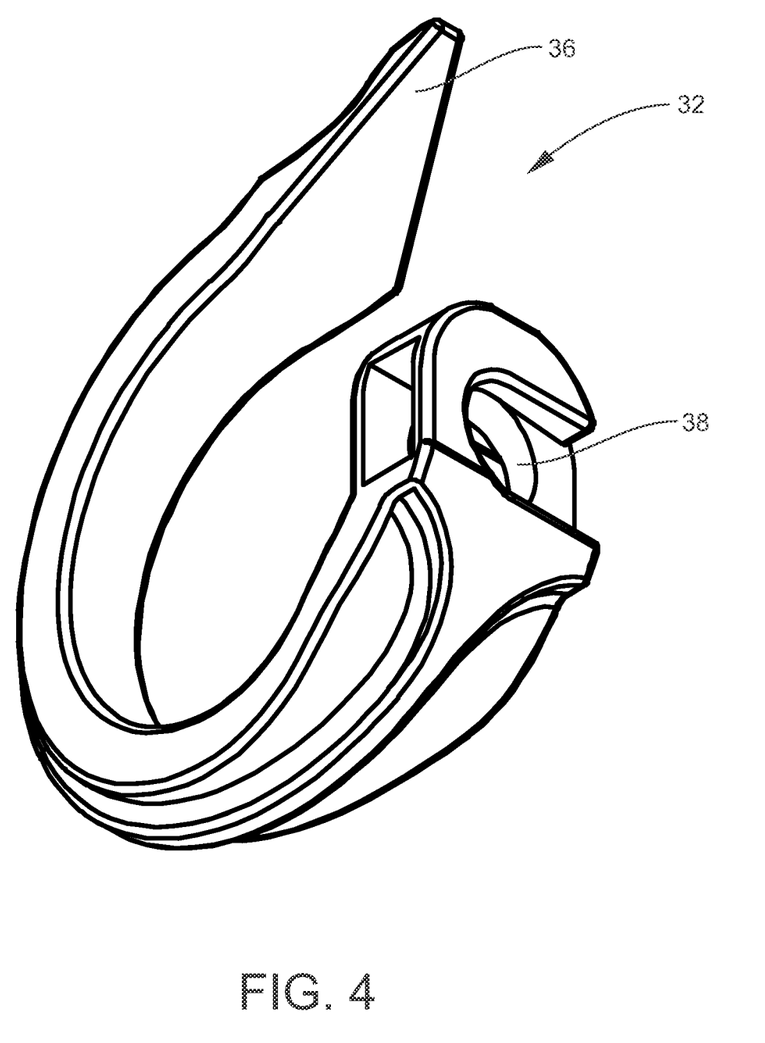
FIG. 4 is a perspective view of the first portion of the hanging mechanism.
Figure 5:
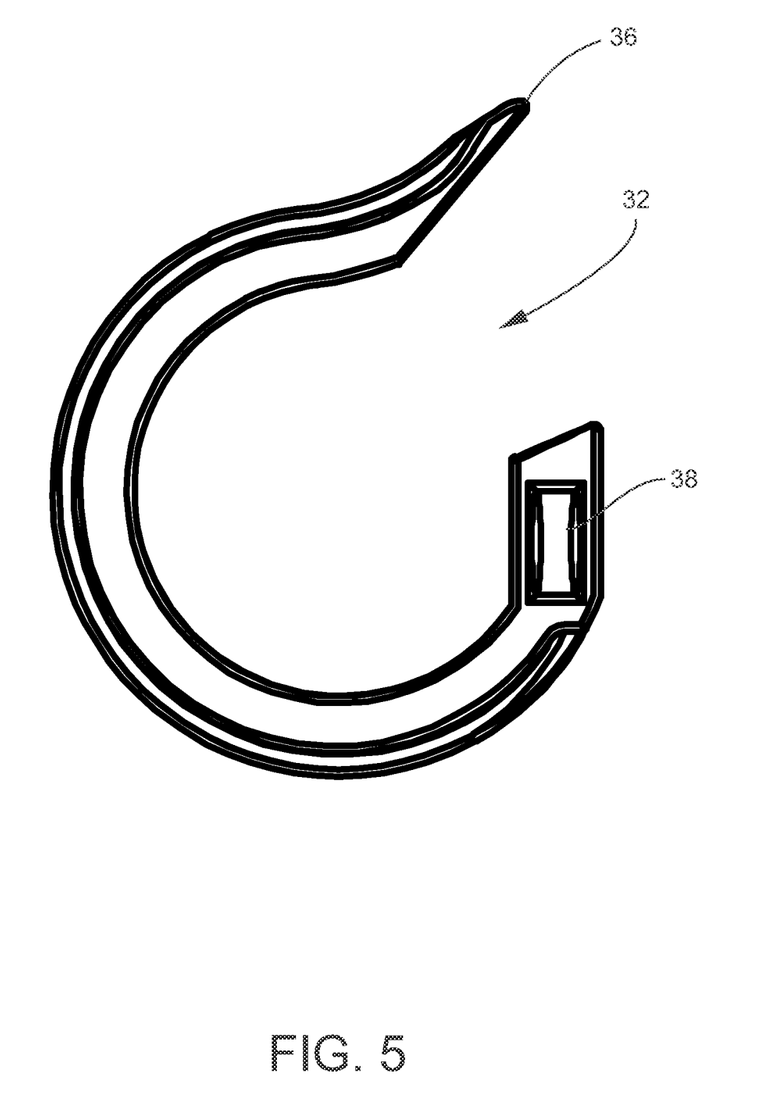
FIG. 5 is a side view of the first portion of the hanging mechanism.

Referring now specifically to the drawings, an air scent device is illustrated in FIG. 1 and is shown generally at reference numeral 10. The device 10 contains a base 12 that extends to an outer edge having a top portion and a bottom portion. The base 12 may have any configuration, but as illustrated, the base 12 is generally circular in shape. An annular outer ring 14 extends substantially upwardly from the outer edge of the base 12. As illustrated in FIG. 1, the annular ring 14 contains an upper portion and a lower portion. The lower portion is adjacent the outer edge of the base 12 and the upper portion engages and outer lip 16 that extends from the upper portion of the annular ring 14. The outer lip 16 extends generally outwardly and slopes downwardly. The outer lip 16 contains a top portion and a bottom portion, whereby the top portion may contain concentric raised edges 18 disposed thereon.

The top portion of the base 12 includes a plurality of upwardly extending protruding structures 20. The protruding structures 20 have a first side and a second side, whereby the first side is engaged to the base 12 of the device 10 and extends generally upwardly towards the second side. The protruding structures 20 may have a constant diameter. On the other hand, the second side may contain a top portion that extends perpendicularly with respect to the protruding structure 20. A scented substance, such as a scented gel 22, is disposed within the base with the protruding structures 20 dispersed therein. The alternative top portion of the protruding structure assists with retaining the scented gel 22 within the base 12. The second side of the protruding structure 20 may extend above the upper level of the scented gel 22. The protruding structures 20 serve the purpose to retain the scented gel 22 within the cavity 14 and to prevent a user's fingers from contacting the scented gel 22 when handing the device 10. The scented gel 22 may be dyed to produce a colored scented gel 22.

The device 10 may be attached to a filter, air duct, or other retention device for retaining the device 10 within the flow of air. To assist with attachment, the device 10 contains at least one clip 24 positioned within the outer lip 16. Preferably, and as illustrated, the device 10 may contain four clips 24 for providing multiple arrangements for the device 10 to be attached to a filter, air duct, or the like. As illustrated, the clips 24 may be spaced an equal distance apart around the outer lip 16.

The clip 24 has a generally semi-circular shape and is attached to the outer lip 16 by a biasing member 26. The biasing member 26 is engaged to the clip 24 and the bottom portion of the outer lip 16 of the device 10 for allowing the clip 24 to pivot between a first position and a second position. In the first position, the clip 24 is flush with the outer lip 16. In the second position, the clip 24 is rotated downwards, thus separating the clip 24 from the outer lip 16. Therefore, in the second position, the clip 24 is in a spaced-apart relationship with the outer lip 16, creating a space between the clip 24 and outer lip 16 for inserting a portion of the filter frame. The biasing member 26 of the clip is biased forward towards the first position, creating a selectively secured relationship between the clip 24 and frame of the filter.

Figure 7:
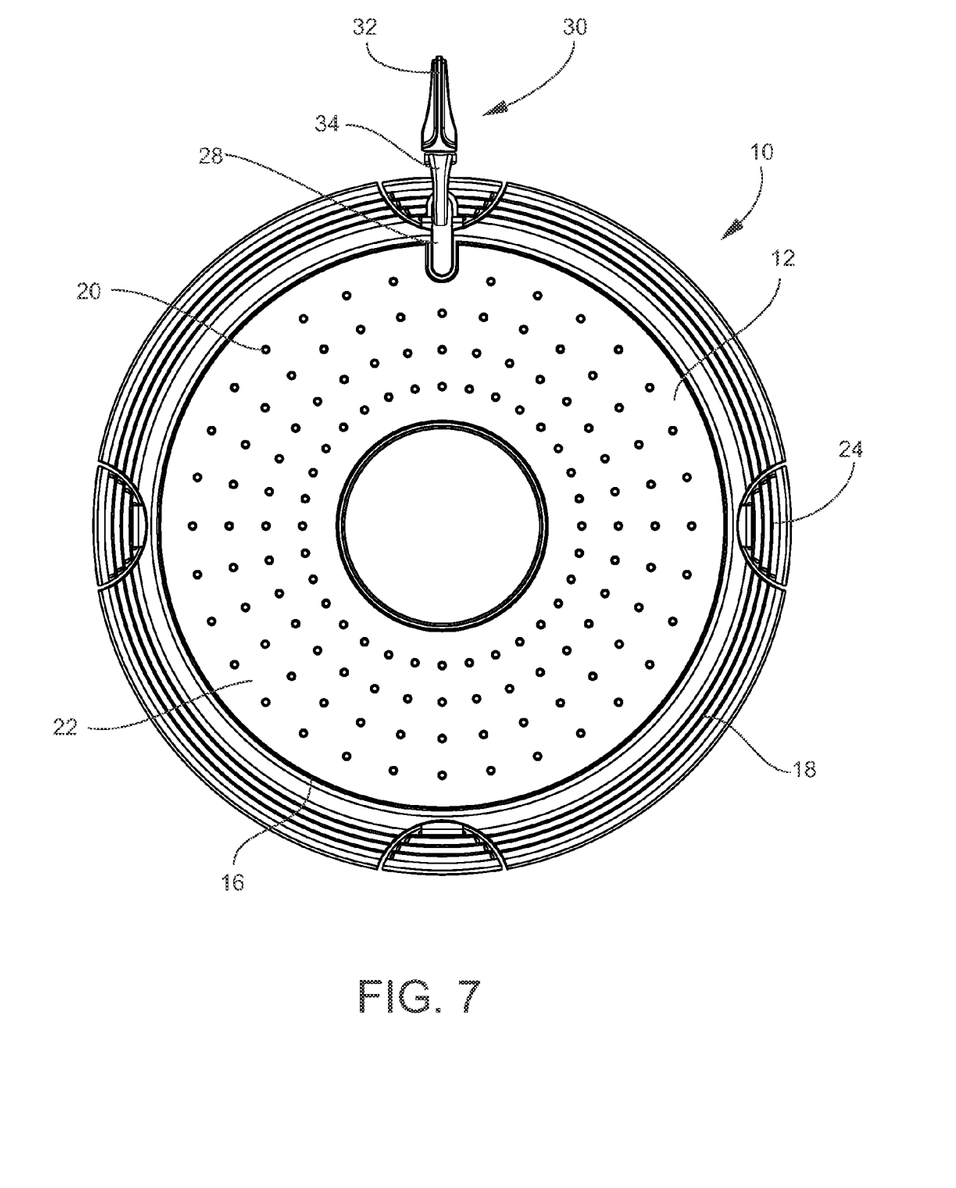
FIG. 7 is a perspective view of the present invention engaged to the hanging mechanism.

A slot 28 may be disposed on the device 10. As illustrated in FIG. 7, the slot 28 may extend from the central portion of the clip 24, and from the top portion to the bottom portion of the outer lip 16. The slot 28 additionally extends into the base 12. The annular ring 14 extends within the base and forms the bottom portion of the slot 28 and partitions the base 12 from the slot 28.

The slot 28 is designed to receive a hanging mechanism 30, as shown in FIGS. 4-7. The hanging mechanism 30 contains a first portion 32 and second portion 34, with the first portion 32 and second portion 34 being generally c-shaped and being selectively secured to one another. The first portion 32 has a first end and a second end. The first end of the first portion 32 contains a pointed section 36 and the second end contains a circular bore 38. The pointed section has a gradually decreasing diameter that ends at a point. Additionally, a ridge runs down the outside exterior side of the first portion 32.

Figure 6:
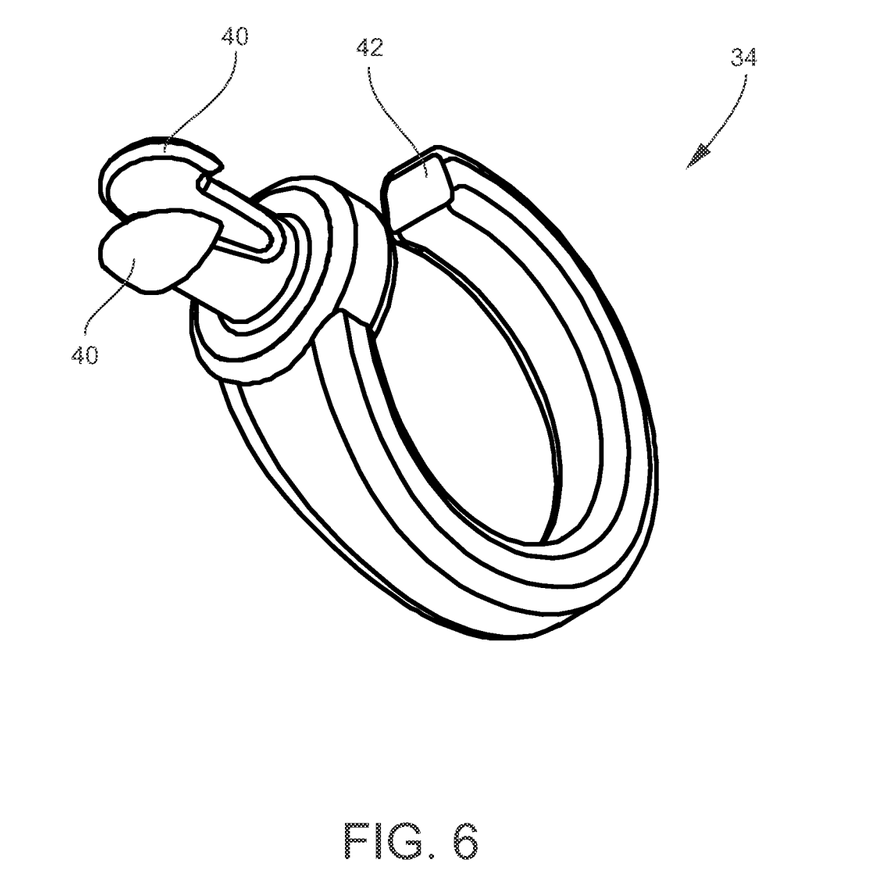
FIG. 6 is a perspective view of the second portion of the hanging mechanism.

The second portion 34 of the hanging mechanism 30 contains a first end and a second end. The first end of the second portion 34 contains at least a pair of resiliently flexible fingers 40 and the second end contains a retention end 42. The resiliently flexible fingers 40 extend outwardly from first end for receipt within the bore 38 of the second end of the first portion 32 for forming a selectively secured arrangement. Alternatively, the first end may contain a plurality of resiliently flexible fingers. The retention end 42 is inserted within the slot 28 and the first end of the first portion 32 is hung from a duct, vent, louver, air filter or the like and within the stream of air flow.

The device 10 as illustrated is generally circular. However, the device may be generally rectangular, generally square, or any other shape desired by the user. The device 10 may be composed of many materials, such as plastic, rubber, metal, and the like. The scented gel is composed of about 10 to about 40 percent PVC copolymer and from about 60 to about 90 percent dicarboxylic acid ester, and preferably from about 15 to about 25 percent PVC copolymer and from about 65 to about 85 dicarboxylic acid ester, and more preferably from about 20 to about 25 percent PVC copolymer and from about 75 to about 80 percent dicarboxylic acid ester.

The central portion of the cavity 14 may contain a raised central portion. The raised central portion allows a trade name or other identifier to be placed on the device 10. The raised portion may contain a scented gel 22 over this portion, or the raised portion may not contain the scented gel 22.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention and are intended to be covered by the following claims.

What is claimed is:

1. An air scent device, comprising:
   a base that extends to an outer edge;
   an outer ring that extends substantially upwardly from the outer edge;
   an outer lip that extends substantially outwardly from the outer ring;
   a scented gel disposed within the base,
   at least one clip positioned within the outer lip and engaged to the outer lip by a biasing member, wherein the clip may pivot between a first position and a second position, in the first position the clip is flush with the outer lip, and in the second position, the clip is in a spaced apart relationship with the outer lip;
   a hanging mechanism having a generally c-shaped first portion having a first end and a second end and a generally c-shaped second portion having a first end and a second end, the first portion and the second portion are selectively secured to each other, the first end of the first portion contains a pointed section and the second end of the first portion contains a circular bore, the first end of the second portion contains at least a pair of resiliently flexible fingers and the second end of the second portion contains a retention end, whereby the resiliently flexible fingers are inserted into the bore of the second end of the first portion; and
   a plurality of protruding structures having a constant diameter and extending substantially upwardly from the base and through the scented substance.

2. The air scent device of claim 1, further comprising a plurality of ridges disposed on the outer lip.

3. The air scent device of claim 1, wherein the base is generally circular.

4. The air scent device of claim 1, wherein the clip is generally semi-circular in shape.

5. The air scent device of claim 1, further comprising four clips spaced an equal distance apart around the outer lip.

6. The air scent device of claim 1, wherein the outer lip has a top portion and a bottom portion, whereby the outer lip slopes downwardly with respect to the outer ring.

7. The air scent device of claim 1, further comprising a slot within the clip.

8. An air scent device, comprising:
   a generally circular base that extends to an outer edge having a generally circular cavity with a raised central portion within the cavity;
   a generally circular outer ring that extends substantially upward from the outer edge;
   a generally circular outer lip that extends substantially outwardly from the outer ring;
   a clip;
   a gel disposed within the generally circular cavity and not on the raised central portion within the cavity;
   a hanging mechanism having a generally c-shaped first portion having a first end and a second end and a generally c-shaped second portion having a first end and a second end, the first portion and the second portion are selectively secured to each other, the first end of the first portion contains a pointed section and the second end of the first portion contains a circular bore, the first end of the second portion contains at least a pair of resiliently flexible fingers and the second end of the second portion contains a retention end, whereby the resiliently flexible fingers are inserted into the bore of the second end of the first portion; and
   a plurality of protruding structures that extend substantially upward from the base and through the gel.

9. The air scent device of claim 8, wherein the gel is dyed.

10. The air scent device of claim 8, wherein the gel is scented.

11. The air scent device of claim 8, wherein the clip contains raised ridges.

12. The air scent device of claim 8, wherein the protruding structure is cylindrical in shape and having a constant diameter.

13. The air scent device of claim 8, further comprising a raised central portion that does not contain the gel.

14. An air scent device, comprising:
   a circular base that extends to an outer edge having a generally circular cavity;
   an outer ring that extends substantially upward from the outer edge;
   an outer lip that extends substantially outwardly from the outer ring and having a bottom portion;
   a plurality of protruding structures that have a constant diameter and extending substantially upwardly from the base;
   a clip containing a biasing member for moving the clip from a first position to a second position and having a central portion;
   a slot extending from the central portion of the clip to the bottom portion of the outer lip;
   a hanging mechanism containing a generally c-shaped first portion having a first end and a second end and a generally c-shaped second portion having a first end and a second end, the first portion and the second portion are selectively secured to each other, the first end of the first portion contains a pointed section and the second end of the first portion contains a circular bore, the first end of the second portion contains at least a pair of resiliently flexible fingers and the second end of the second portion contains a retention end, whereby the resiliently flexible fingers are inserted into the bore of the second end of the first portion and the retention end is inserted within the slot; and
   a scented gel disposed within the generally circular cavity, wherein the plurality of protruding structures extend through the gel.

15. The air scent device of claim 14, further comprising four clips spaced an equal distance apart around the outer lip.

16. The air scent device of claim 14, wherein the outer lip has a top portion and a bottom portion, whereby the outer lip slopes downwardly with respect to the outer ring.

17. The air scent device of claim 14, further comprising a hanging mechanism comprising a first portion and second portion, the first portion and second portion are substantially c-shaped and the first portion is selectively secured to the second portion.

\* \* \* \* \*